United States Patent
Drovetskaya et al.

(10) Patent No.: US 9,592,187 B2
(45) Date of Patent: Mar. 14, 2017

(54) EASILY FORMULATED ZINC OXIDE POWDER

(71) Applicant: BASF SE, Ludwigshafen (DE)

(72) Inventors: Tatiana Drovetskaya, Martinsville, NJ (US); Marc N. G. De Mul, Weston, CT (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/400,004

(22) PCT Filed: May 14, 2013

(86) PCT No.: PCT/US2013/040949
§ 371 (c)(1),
(2) Date: Nov. 10, 2014

(87) PCT Pub. No.: WO2013/173336
PCT Pub. Date: Nov. 21, 2013

(65) Prior Publication Data
US 2015/0147362 A1   May 28, 2015

Related U.S. Application Data

(60) Provisional application No. 61/647,099, filed on May 15, 2012.

(51) Int. Cl.
| | | |
|---|---|---|
| A61K 8/49 | (2006.01) | |
| A61K 8/27 | (2006.01) | |
| A61Q 17/04 | (2006.01) | |
| A61K 8/891 | (2006.01) | |
| A61K 8/02 | (2006.01) | |

(52) U.S. Cl.
CPC .......... *A61K 8/4966* (2013.01); *A61K 8/0241* (2013.01); *A61K 8/27* (2013.01); *A61K 8/891* (2013.01); *A61Q 17/04* (2013.01); *A61K 2800/412* (2013.01); *A61K 2800/624* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,032,390 A | 7/1991 | Iwaya et al. | |
| 5,200,595 A | 4/1993 | Boulos et al. | |
| 5,460,701 A | 10/1995 | Parker et al. | |
| 5,486,631 A | 1/1996 | Mitchnick et al. | |
| 5,514,349 A | 5/1996 | Parker et al. | |
| 5,575,988 A | 11/1996 | Knowles et al. | |
| 5,756,788 A | 5/1998 | Mitchnick et al. | |
| 5,874,684 A | 2/1999 | Parker et al. | |
| 6,045,650 A | 4/2000 | Mitchnick et al. | |
| 6,083,490 A * | 7/2000 | Ellis | A61K 8/044 424/401 |
| 6,203,768 B1 | 3/2001 | McCormick et al. | |
| 6,267,949 B1 * | 7/2001 | Halls | A61K 8/27 106/14.34 |
| 6,409,998 B1 | 6/2002 | Candau et al. | |
| 6,669,823 B1 | 12/2003 | Sarkas et al. | |
| 7,348,029 B2 * | 3/2008 | Kliss | A61K 8/044 424/489 |
| 7,517,513 B2 | 4/2009 | Sarkas et al. | |
| 2003/0161795 A1 | 8/2003 | Tsuzuki et al. | |
| 2006/0058444 A1 | 3/2006 | Dransfield et al. | |
| 2011/0150792 A1 | 6/2011 | Shao et al. | |

FOREIGN PATENT DOCUMENTS

| | | |
|---|---|---|
| CN | 102246014 A | 11/2011 |
| EP | 0 957 139 A1 | 11/1999 |
| EP | 1093796 A1 | 4/2001 |
| EP | 2 703 351 A1 | 3/2014 |
| WO | 9323482 A1 | 11/1993 |
| WO | 9852525 A1 | 11/1998 |
| WO | 2006/024633 A1 | 3/2006 |
| WO | 2006/105600 A1 | 10/2006 |
| WO | 2012/168102 A2 | 12/2012 |

OTHER PUBLICATIONS

Horiba, A guide to Particle Size Analysis, 2014, pp. 3-5.*
NanoComposix Nanocomposix's Guide to Dynamic Light Scattering Measurement and Analysis, Guidelines for Dynamic Light Scattering Measurement and Analysis, v. 1.4, 2015, pp. 1-8.*
Lavernia et al. On the analysis of grain size in bulk nanocrystalline materials via x-ray diffraction, Metallurgical and Materials Transactions, 2003, vol. 34 A, pp. 1349-1355.*

(Continued)

*Primary Examiner* — Bethany Barham
*Assistant Examiner* — Ping Cao
(74) *Attorney, Agent, or Firm* — Lowenstein Sandler LLP

(57) ABSTRACT

The present disclosure relates to polymeric siloxane coated zinc oxide powders having a mean particle size number distribution (D50) ranging from about 300 nm to about 600 nm and their use in sunscreen compositions. The relatively high surface area (in relation to particles of <100 nm) avoids agglomeration resulting in ease of formulation and high dispersal of the particles which tends toward less light scatter and hence better transparency in formulations. Furthermore, the combination of the particular particle size number distribution (D50) of zinc oxide ranging as above with bis(resorcinyl)triazine UV absorbers shows unexpected increased UV-A absorbance (320 to 400 nm) in comparison to the zinc oxide and bis resorcinyl triazine UV absorbers on their own at the same concentration.

11 Claims, No Drawings

(56) References Cited

OTHER PUBLICATIONS

Faure et al., Dispersion and surface functionalization of oxide nanoparticles for transparent photocatalytic and UV-protecting coating and sunscreens, Sci. Technol. Adv. Mater. 2013, vol. 14, pp. 1-23.*
International Search Report and Written Opinion dated Aug. 19, 2013.
The Extended European Search Report on Application No. 13791037.8-1460, mailed on Feb. 26, 2016.

* cited by examiner

EASILY FORMULATED ZINC OXIDE POWDER

FIELD OF THE INVENTION

The present invention relates to polymeric siloxane coated zinc oxide powders having a mean particle size number distribution ($D_{50}$) ranging from about 300 nm to about 600 nm. The zinc oxide powder comprises zinc oxide discrete particles with no durable secondary structure or aggregation when dispersed in formulations. The dispersions result in high transparency within dispersion and on skin. The high surface area of the particles avoids agglomeration resulting in ease of formulation. Furthermore, the combination of the polymeric siloxane coated zinc oxide powders with bis (resorcinyl) triazine UV absorbers shows unexpected improved absorbance in the UV-A (320 to 400 nm) range.

BACKGROUND

The use of zinc oxide as a sunscreen is well known in the art. It has excellent UV screening capability which covers the full range of UVA and UVB wavelengths. It is also considered one of the safest and most trusted UV actives. Additionally, it is highly light stable and shows virtually no degradation on exposure to light.

For example, U.S. publication number 20030161795 and U.S. Pat. No. 5,032,390 describe zinc oxide particles for use in shielding the skin from ultraviolet radiation relying on physical UV screening agents alone such as zinc oxide.

Furthermore, it is well known to coat zinc oxide in order to provide it with a hydrophobic coating improving the feel on skin and helping to disperse the particles within various formulations.

In particular U.S. Pat. Nos. 6,045,650, 5,486,631, 5,756,788 describe siloxane treated metal oxides resulting in a hydrophobic metal oxide which is non-reactive, unaffected by water and can be applied to the skin for protection from ultraviolet light of the sun. PCT application 2006/1 05600 also teaches the coating of metal oxide particles via treatment of the metal oxide particles with an aqueous solution of water-soluble organosilicon monomers and initiating polymerization.

The above cited patents and application are concerned with nano sized particles, that is particles which are characterized by a size of less than 100 nm. Particles of zinc oxide in particle size ranges above 100 nm are known to cause a whitening effect on the skin. The very small particle size zinc oxide (<100 nm) allows for the incorporation of significant amounts of zinc oxide while maintaining formulation transparency on skin, a highly desirable effect.

However, in recent years the public and regulatory agencies have expressed concern regarding the use of nanoparticles (particles <100 nm) in personal care formulations. Questions relating to their absorbance into skin, their ability to impact at the cellular level and their intrinsic toxicity versus that of their macro counterparts are being considered. No definitive answers are presently available.

Additionally, the formulation of nano zinc oxide particle (<100 nm) provides numerous challenges. The surface area is extremely large and even with adequate coating of the oxide with hydrophobic materials, the particles tend to agglomerate requiring additional cost and processing steps to fully disperse to ensure that the particles apply evenly as sun screen. It is important to provide particles which are more easily dispersed.

Accordingly, there is still a need for zinc oxide particles which are of an acceptable whitening effect in formulation but of a particle size distribution which excludes particles smaller than 100 nm.

Furthermore, numerous studies in recent years have shown that ultraviolet radiation in the wavelength range from 320 to 400 nm (UV-A range) makes a significant contribution to the skin damage caused by sunlight. Therefore there is an increasing requirement for adequate protection against UV-A radiation. In addition, the availability of sun protection preparations having a high sun protection factor (hereinafter also referred to as SPF) has led to concerns that users are able to stay in the sun for longer and, as a result, are exposed to an increased amount of UV-A radiation.

Accordingly it would be highly desirable to achieve higher UV-A absorbance in combination with zinc oxide particles of a size distribution which excludes particles smaller than 100 nm.

SUMMARY OF THE INVENTION

The Applicants have solved the above needs for higher UV-A absorbance and avoidance of nanoparticles.

The Applicants have discovered that a zinc oxide particle defined by a particular particle size distribution and no durable secondary structure or aggregation, offers excellent formulation ease and acceptable whitening effects in sunscreen formulations.

Accordingly the invention is directed to a sunscreen composition comprising:
  a) a zinc oxide particle defined by a mean particle size (volume) distribution-D50 of about 400 nm to about 650 nm, preferably about 450 to about 625 and most preferably about 475 nm to about 600 nm, measured by Dynamic Light Scattering (DLS), the particle is hexagonal zincite crystal structure, and 0.0% zinc oxide particles in the distribution are below 100 nm wherein the % is based on the number of particles in the distribution
  b) optionally a cosmetically acceptable adjuvant.

Additionally, a concentrated dispersion is encompassed by the invention which comprises
a) zinc oxide particles defined by a mean particle size (volume) distribution-D50 of about 400 nm to about 650 nm, preferably about 450 to about 625 and most preferably about 475 nm to about 600 nm, measured by Dynamic Light Scattering (DLS), the particle is hexagonal zincite crystal structure, and 0.0% zinc oxide particles in the distribution are below 100 nm wherein the % is based on the number of particles in the distribution
and
b) a carrier selected from the group consisting of di- or tri-glycerides, based on $C_6$-$C_{18}$ fatty acids Di- or tri-glycerides, modified by reaction with other alcohols (caprylic/capric triglyceride, wheat germ glycerides, etc.), fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil and borago oil, preferably di- or tri-glycerides, based on $C_6$-$C_{18}$ fatty acids Di- or tri-glycerides, modified by reaction with other alcohols (caprylic/capric triglyceride, wheat germ glycerides, etc.), wherein the weight percent of the zinc oxide particles make up at least about 50 to about 90, preferably about 60 to about 80 weight percent of the total weight of the concentrated dispersion.

Further, a method of formulating a sunscreen composition is envisioned by adding the above zinc oxide particle to a cosmetically acceptable carrier.

Use of the above zinc oxide particles of the defined D50 (volume) above for formulation of sunscreens compositions is also envisioned.

And lastly, combinations of the above zinc oxide particles with particular sunscreen actives such as bis(resorcinyl) triazines in combination with the zinc oxide powder of the invention are envisioned either in sunscreen or in the above concentrated dispersion.

DETAILED DESCRIPTION OF THE INVENTION

The term "comprising" for purposes of this application means that the term is used inclusively, in the sense that there may be other features and/or steps included in the invention not expressly defined or comprehended in the features or steps subsequently defined or described.

The term "cosmetically acceptable carrier" means hydrophobic liquid suitable for skin contact. Such suitable carriers would for example be liquid silicones or polyorganosiloxanes, mineral oils, hydrogenated polyisobutene, polydecene, paraffins, isoparaffins of at least 10 carbon atoms, and aliphatic or aromatic ester oils (e.g. isopropyl myristate, lauryl myristate, isopropyl palmitate, diisopropyl sebecate, diisopropyl adipate, or $C_8$ to $C_{18}$ alkyl benzoates), cocoglycerides, caprylic/capric triglycerides, propylheptyl caprylate, dicaprylyl carbonate, ethylhexyl palmitate and ethylhexyl octanoate. Water for example is excluded from the term "cosmetic acceptable carrier". Although, water may also be formulated with the cosmetic acceptable carrier. For example, the cosmetic acceptable carrier may be an oil and water or a water in oil emulsion.

The hydrophobic liquid suitable for skin contact may be selected from the group listing above.

Zinc Oxide

Zinc oxide for purposes of this application may be obtained by any means known in the art. For example U.S. Pat. No. 6,203,768 uses mechano-chemical process to form zinc oxide. Mechano-chemical processing involves a mechanically activated chemical reaction between a precursor metal compound and a suitable reactant during mechanical milling or during subsequent heat treatment of the milled powder. U.S. Patent Pub. No. 2003/0161795 describes in detail various mechano-chemical processes in paragraphs [00730 through [0081] and example 1.

However, it is highly preferable that the zinc oxide of the present application be formed directly from zinc metal fed into a plasma arc. The metal is then vaporized and oxygen is added to produce zinc oxide which upon cooling condenses to form nanocrystalline zinc oxide.

The zinc oxide is therefore preferably formed directly as a dry powder. It is not milled, precipitated or derived from organic precursors (fumed). Because of this, the particle surfaces are very "clean" chemically, which makes it straightforward to obtain dispersions with excellent stability over time. Also, there are fewer impurities which impact the color of the final material.

The plasma used to produce the zinc oxide may be for example DC plasma arc, RF plasma, electric heating, conductive heating, flame reactor, induction plasma or laser reactor.

The plasma generation of particles is well known in the art. In particular, U.S. Pat. Nos. 5,200,595, 6,669,823 and 7,517,513 teach the use of plasma systems for generating well controlled inorganic particles. Further, U.S. Pat. Nos. 5,460,701, 5,514,349 and 5,874,684 are also excellent references for reviewing controlled generation of inorganic particulates without aggregation using a plasma arc.

Mean Particle Size Distribution

Mean particle size distribution is often abbreviated D50. The mean particle size deviation may be a Number or a Volume distribution. When the term "mean particle size distribution" used in the present application, unless otherwise specified, the D50 is based on volume.

Measurements of the mean particle size distribution are dependent upon the method of measurement. Different measurements will arrive at different values. For example, average particle size may be calculated from BET (N2 adsorption), Static Light Scattering or Dynamic Light Scattering. The D50 (Volume) determination used by the Applicants is based on Dynamic Light Scattering (DLS) using a Malvern® Nano ZS instrument.

The zinc oxide particles taught herein have a mean particle size (volume) distribution-D50 of about 4 nm to about 650 nm, preferably about 450 to about 625 and most preferably about 475 nm to about 600 nm, measured by Dynamic Light Scattering (DLS). Because the size distribution is highly controlled with virtually no particles falling below 100 nm, the zinc oxide particles form excellent dispersions of the primary particles (no agglomeration), which translates into higher transparency in formulation.

As explained above it is highly preferred that virtually no particles of <100 nm make up the mean particle distribution. By no particles of <100 nm it is meant that 0.0% of particles fall below 100 nm. The percent is based on the total Number distribution.

Morphology of Zinc Oxide

The zinc oxide particle crystal structure is zincite (hexagonal) determined by X-ray diffraction.

The crystal morphology is elongated. This is not the same as rods or rod-like but the crystals have a low aspect ratio evident from transmission electron micrographs.

The average crystal size ($D_{XRD}$) of the zinc oxide varies from about 150 nm to about 350 nm, preferably about 175 nm to about 320 nm, more preferably about 200 nm to about 300 nm.

Secondary Structure or Aggregation

There is substantially no secondary structure or aggregation of the present zinc oxide particles. The term "secondary structure or agglomeration" means for purposes of this application that the particles are discrete. Small particles are not bound to form a composite aggregate.

In the dry state the particles do agglomerate. However, the particles are dispersed to primary particles with proper treatment in fluids.

Thus the sunscreen composition will preferably further contains a cosmetically suitable carrier, preferably hydrophobic and the zinc oxide particles are well dispersed in said carrier so that discrete particles with no secondary structure are evident.

Aggregation or secondary structure is difficult to avoid in nanomaterials particularly coated nanomaterials. Nanomaterials will likely aggregate during processing especially if produced by mechano-chemical processes, colloidal precipitation, mechanical grinding followed by coating or hydrophobic treatment resulting in aggregates which are bound together by the coating.

However nanosized powders which are used in the present application are preferably produced by vaporization and gas phase nucleation (plasma systems) and growth. This makes it possible to generate nanoparticles with controlled size distribution of the primary particles and control the degree of aggregation by controlling process parameters such as pressure, temperature, and concentration that aid in the determination of the properties of the resulting particles.

Treatment of the Zinc Oxide Particles

The zinc oxide particles is by its nature hydrophilic, which makes the particles non-wettable with organic solvents, oils and plastics that are frequently used as carrier media in the cosmetic or sunscreen applications. Furthermore zinc oxide has high photo-activity, which may result in undesired effects caused by reactions between the metal oxides and other components in the sunscreen or cosmetic.

Additionally nanosized zinc oxide may also have high surface reactivity, which leads to increased interactions between neighboring particles. Over time this can result in flocculation of the particles in the formulation.

A generally accepted method of overcoming such problems has been to surface coat the metal oxide particles to render them hydrophobic.

Organosilicon compounds such as silicone and polysiloxane have been used to surface treat metal oxide powders in an attempt to overcome this problem. Silicones are polymers that have a regular repeating backbone of —Si—O— and contain side groups of varying functionality. Most notably, organosilicon compounds containing methyl side group (dimethyl polysiloxanes), methyl and hydrogen side groups (methyl hydrogen polysiloxanes), and alkyl groups (alkyl polysiloxanes) have been utilized. Additionally, the side groups of the silicone may be selected to match the chosen carrier media to enable a greater affinity between the surface treated powders and the carrier media. Several prior art techniques have been developed for coating metal oxide fine particles with silicone or organosilicon. For example, organosilicon polymers in solvents or directly onto the dried powder have been used to coat zinc oxide particle. Additional organosilicon monomers or oligomers can be applied to the dried powder or the dispersed powder and then polymerized.

It is preferable that the dried powder or dispersed powder is treated with monomers or oligomers which polymerize in the presence of the particles. This controls agglomeration and is more likely to completely coat each discrete particle. Of particular interest are trialkoxyalkly silane monomers which polymerize to form a polyalkylsilsesquioxane coating. For example triethoxyoctyl silane monomer may be polymerized to form a polysilsesquioxane coating on the zinc oxide. This monomer upon polymerization forms a polysilsesquioxane, in particular a poly-n-octylsilsesquioxane or polycaprylsilsesquioxane which is a preferred coating for the zinc oxide.

The weight percent of the coating or surface treatment of the zinc oxide ranges from 0.01 to about 5 wt. %, preferably about 0.1 to about 3 wt. %, and most preferably about 0.2 to about 2 wt. % based on the coated zinc oxide.

Zinc Oxide Cosmetic Sunscreen Preparations

Of special importance as sunscreen preparation are light-protective preparations for the skin, such as sun milks, lotions, creams, oils, sunblocks or tropicals, pretanning preparations or after-sun preparations. Of particular interest are sun protection creams, sun protection lotions, sun protection milk and sun protection preparations in the form of a spray.

The cosmetic or sunscreen preparations may be, for example in the form of, creams, gels, lotions, alcoholic and aqueous/alcoholic solutions, emulsions, wax/fat compositions, stick preparations, powders or ointments. In addition to the above mentioned zinc oxide particles, the cosmetic or sunscreen preparations may contain further cosmetically acceptable adjuvants.

Cosmetically acceptable adjuvants are virtually any ingredients which are suitable for skin exposure. Thus the cosmetically acceptable adjuvants are selected from the group consisting of surfactants, super-fatting agents, oils, emulsifiers, consistency regulators, thickeners, polymers, stabilizers, biogenic active ingredients, swelling agents, further UV light-protective agents, antioxidants, hydrotropic agents, preservatives, solubilisers, perfume oils, colourants, bacteria-inhibiting agents and mixtures thereof.

Of particular interest are sunscreen compositions which contain water and oil. For example, W/O, O/W, O/W/O and W/O/W emulsions, or microemulsions. These emulsions may contain, for example, from 0.1 to 30% by weight, preferably from 0.1 to 15% by weight and especially from 0.5 to 10% by weight, based on the total weight of the composition, of one or more UV absorbers in addition to the zinc oxide particles described above, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

Zinc oxide particles of the invention may be added to cosmetics or sunprotective compositions including sunscreen compositions at virtually any amount. For example the weight percent of the zinc oxide particles in a cosmetic, sunprotective composition including sunscreen compositions will vary from about 0.01 to about 25 weight percent, preferably 0.1 to about 20 weight percent, most preferably 1.0 to about 15 weight percent wherein the weight percent is based on the total weight of the formulation.

The cosmetic or sunscreen compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants

Diethylhexyl 2,6-naphthalate, di-n-butyl adipate, di(2-ethylhexyl)-adipate, di(2-ethyl hexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially lauryl and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Emulsifiers

Any conventionally usable emulsifier can be used for the compositions. Emulsifier systems may comprise for example: carboxylic acids and their salts: alcalin soap of sodium, potassium and ammonium, metallic soap of calcium or magnesium, organic basis soap such as Lauric, palmitic, stearic and oleic acid etc. . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block (oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkyl betaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Nonionic bases such as PEG-6 beeswax (and) PEG-6 stearate (and) polyglyceryl-2-isostearate, glyceryl stearate (and) PEG-100 stearate, PEG-5 glyceryl stearate, sorbitan oleate (and) polyglyceryl-3 ricinoleate, sorbitan stearate and sucrose cocoate, glyceryl stearate and laureth-23, cetearyl alcohol and ceteth-20, cetearyl alcohol and colysorbate 60 and PEG-150 and stearate-20, cetearyl alcohol and cetearyl polyglucoside, cetearyl alcohol and ceteareth-20, cetearyl alcohol and PEG-40 castor oil, cetearyl alcohol and PEG-40 castor oil and sodium cetearyl sulfate, stearyl alcohol and steareth-7 and steareth-10, cetearyl alcohol and szeareth-7 and steareth-10, glyceryl stearate and PEG-75 stearate, propylene glycol ceteth-3 acetate, propylene glycol isoceth-3 acetate, cetearyl alcohol and ceteth-12 and oleth-12, PEG-6 stearate and PEG-32 stearate, PEG-6 stearate and ceteth-20 and steareth-20, PEG-6 stearate and ceteth-20 and glyceryl stearate and steareth-20, glyceryl stearate and ceteareth-20.

Anionic alkaline bases such as PEG-2 stearate SE, glyceryl stearate SE, propylene glycol stearate. Anionic acid bases such as cetearyl Alcohol and Sodium cetearyl sulfate, cetearyl alcohol and sodium lauryl sulfate, trilaneth-4 phosphate and glycol stearate and PEG-2 stearate, glyceryl stearate and sodium lauryl Sulfate. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic sunscreen compositions, for example creams, gels, lotions, alcoholic and aqueous/alcoholic solutions, emulsions, wax/fat compositions, stick preparations, powders or ointments, may in addition contain, as further adjuvants and additives such as, mild surfactants, super-fatting agents, consistency regulators, thickeners, polymers, stabilisers, biogenic active ingredients, swelling agents, further UV light-protective factors, antioxidants, hydrotropic agents, preservatives, self-tanning agents, solubilisers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, .alpha.-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (CARBOPOL types 980, 981, 1382, ETD 2001, ETD2020, ULTREZ 10) or SALCARE range such as SALCARE SC80 (steareth-10 allyl ether/acrylates copolymer), Salcare SC81 (acrylates copolymer), Salcare SC91 and Salcare AST (sodium acrylates copolymer/PPG-1 trideceth-6), SEPIGEL 305 (polyacrylamide/laureth-7), SIMULGEL NS and SIMULGEL EG (hydroxyethyl acrylate/sodium acryloyldimethyl taurate copolymer), STABILEN 30 (acrylates/vinyl isodecanoate crosspolymer), PEMULEN TR-1 (acrylates/C10-30 alkyl acrylate crosspolymer), LUVIGEL EM (sodium acrylates copolymer), ACULYN 28 (acrylates/beheneth-25 methacrylate copolymer), etc.

Polymers

As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the sunscreen composition.

Particularly preferred antioxidants are those of the Tinogard® line available from BASF. For example, Tinogard® TT (pentaaerythrityl tetra-di-t-butyl hydroxyhydrocinnamate) and Tinogard® TL (Benzotriazolyl Dodecyl p-Cresol)

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Farbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Additional UV Screening Agents

Sun screening agents which may be combined with the zinc oxide particles in the sunscreen compositions described above would include a range of organic UV screening agents selected from the group consisting of 1(+/−)-1,7,7-trimethyl-3-[(4-methylphenyl)methylene]bicyclo-[2.2.1]heptan-2-one; p-methyl benzylidene camphor,1,7,7-trimethyl-3-(phenylmethylene)bicyclo[2.2.1]heptan-2-one; benzylidene camphor, (2-Hydroxy-4-methoxyphenyl)(4-methylphenyl)methanone, 2,4-dihydroxybenzophenone, 2,2',4,4'-tetrahydroxybenzophenone, 2-Hydroxy-4-methoxy benzophenone, 2-Hydroxy-4-methoxy benzophenone-5-sulfonic acid, 2,2'-dihydroxy-4,4'-dimethoxybenzophenone, 2,2'-Dihydroxy-4-methoxybenzophenone, Alpha-(2-oxoborn-3-ylidene)toluene-4-sulphonic acid and its salts, 1-[4-(1,1-dimethylethyl)phenyl]-3-(4-methoxyphenyl)propane-1,3-dione, Methyl N,N,N-trimethyl-4-[(4,7,7-trimethyl-3-oxobicyclo[2,2,1]-hept-2-ylidene)methyl]anilinium sulphate, 3,3,5-Trimethyl cyclohexyl-2-hydroxy benzoate, Isopentyl p-methoxycinnamate, Menthyl-o-aminobenzoate,2-Ethylhexyl 2-cyano,3,3-diphenylacrylate, 2-ethylhexyl 4-(dimethylamino)benzoate, 2-ethylhexyl 4-methoxycinnamate, 2-ethylhexyl salicylate, Benzoic acid,4,4',4''-(1,3,5-triazine-2,4,6-triyltriimino)tris-, tris(2-ethylhexyl)ester, 4-aminobenzoic acid, Benzoic acid, 4-amino-, ethyl ester, polymer with oxirane, 2-phenyl-1H-benzimidazole-5-sulphonic acid,2-Propenamide, N-[[4-[(4,7,7-trimethyl-3-oxobicyclo[2.2.1]hept-2-ylidene)methyl]phenyl]methyl]-, homopolymer. Triethanolamine salicylate, 3,3'-(1,4-phenylenedimethylene)bis[7,7-dimethyl-2-oxo-bicyclo[2.2.1]heptane-1 methanesulfonic acid], Titanium dioxide, 2,2'-Methylene-bis-[6-(2H-benzotriazol-2-yl)-4-(1,1,3,3-tetramethyl¬butyl)-phenol], Bis-Ethylhexyloxyphenol Methoxyphenyl Triazine,1H-Benzimidazole-4,6-disulfonic acid, 2,2'-(1,4-phenylene)bis-, disodium salt, Benzoic acid, 4,4'-[[6-[[4-[[(1,1-dimethylethyl)amino]carbo¬nyl]-phenyl]amino]1,3,5-triazine-2,4-diyl]diimino]bis-, Phenol, 2-(2H-benzotriazol-2-yl)-4-methyl-6-[2-methyl-3-[1,3,3,3-tetramethyl-1-[(trimethylsily)oxy]disiloxanyl]propyl]-,Dimethicodiethylbenzalmalonate, Benzenesulfonic acid, 3-(2H-benzotriazol-2-yl)-4-hydroxy-5-(1-methyl¬propyl)-, monosodium salt, Benzoic acid, 2-[4-(diethylamino)-2-hydroxybenzoyl]-, hexyl ester, 1-Dodecanaminium, N-[3-[[4-(dimethylamino)benzoyl]amino]-propyl]¬N,N-dimethyl-, salt with 4-methylbenzenesulfonic acid (1:1), 1-Propanaminium, N,N,N-trimethyl-3-[(1-oxo-3-phenyl-2-propenyl)¬amino]-, chloride, 1H-Benzimidazole-4,6-disulfonic acid, 2,2'-(1,4-phenylene)bis-, 1,3,5-Triazine, 2,4,6-tris(4-methoxyphenyl)-,1,3,5-Triazine, 2,4,6-tris[4-[(2-ethylhexyl)oxy]phenyl]-, 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt), 2-Propenoic acid, 3-(1H-imidazol-4-yl)-, Benzoic acid, 2-hydroxy-, [4-(1-methylethyl)phenyl]methyl ester, 1,2,3-Propanetriol, 1-(4-aminobenzoate), Benzeneacetic acid, 3,4-dimethoxy-a-oxo-, 2-Propenoic acid, 2-cyano-3,3-diphenyl-, ethyl ester, Anthralinic acid, p-menth-3-yl ester, 2,2'-bis(1,4-phenylene)-1H-benzimidazole-4,6-disulphonic acid mo¬no sodium salt or Disodium phenyl dibenzimidazole tetrasulfonate, 1,3,5-Triazine-2,4,6-triamine and N,N'-bis[4-[5-(1,1-dimethylpropyl)-2-benzoxazolyl]phenyl]-N''-(2-ethylhexyl).

Of particular interest are bis(resorcinyl)s-triazines UV absorbers having the formula (1) in combination with the zinc oxide above described.

Formula (1) represents a bis resorcinyl s-triazine defined as below.

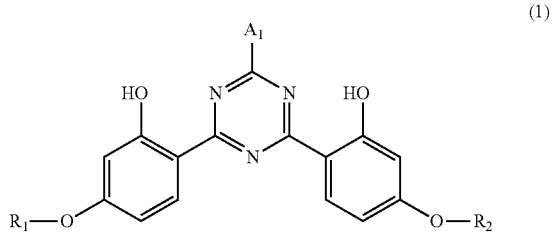

in which $R_1$ and $R_2$, independently of one another, are $C_3$-$C_{18}$alkyl; $C_2$-$C_{18}$alkenyl; a radical of the formula —$CH_2$—CH(—OH)—$CH_2$—O-$T_1$; or $R_1$ and $R_2$ are a radical of the formula

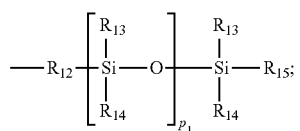
(4a)

$R_{12}$ is a direct bond; a straight-chain or branched $C_1$-$C_4$alkylene radical or a radical of the formula

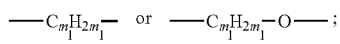

$R_{13}$, $R_{14}$ and $R_{15}$, independently of one another, are $C_1$-$C_{18}$alkyl; $C_1$-$C_{18}$alkoxy or a radical of the formula

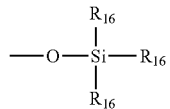

$R_{16}$ is $C_1$-$C_5$alkyl;
$m_1$ and $m_3$, independently of one another, are 1 to 4;
$p_1$ is 0 or a number from 1 to 5;
$A_1$ is a radical of the formula

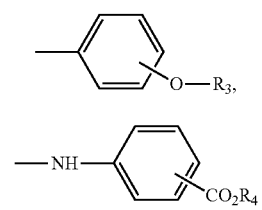
(1b)

(1c)

or of the formula

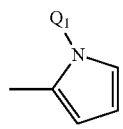
(1d)

$R_3$ is hydrogen; $C_1$-$C_{10}$alkyl, —$(CH_2CHR_5$—$O)_{n_1}$—$R_4$; or a radical of the formula —$CH_2$—$CH($—$OH)$—$CH_2$—$O$-$T_1$;
$R_4$ is hydrogen; M; $C_1$-$C_5$alkyl; or a radical of the formula —$(CH_2)_{m_2}$—$O$-$T_1$;
$R_5$ is hydrogen; or methyl;
$T_1$ is hydrogen; or $C_1$-$C_8$alkyl;
$Q_1$ $C_1$-$C_{18}$alkyl;
M is a metal cation;
$m_2$ is 1 to 4; and
$n_1$ is 1-16.
$C_1$-$C_5$alkyl, $C_1$-$C_{10}$alkyl, $C_1$-$C_{10}$alkyl, and $C_3$-$C_{18}$alkyl are straight-chain or branched alkyl radicals such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl or octadecyl.

$C_2$-$C_{18}$alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

Preferred bis(resorcinyl) compounds of the formula (1) are those in which
$A_1$ is a radical of the formula

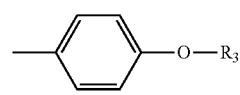
(1a$_1$)

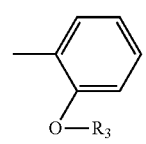
(1a$_2$)

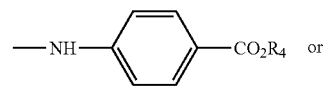
(1b$_1$)

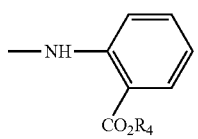
(1b$_2$)

$R_3$ and $R_4$ here are as defined in the formulae (1a) and (1b).

Important bisresorcinyl compounds according to the invention have the formula

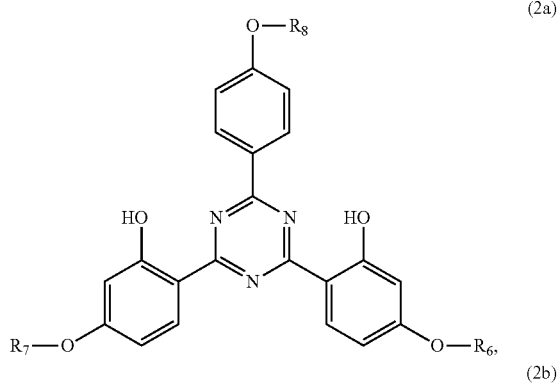
(2a)

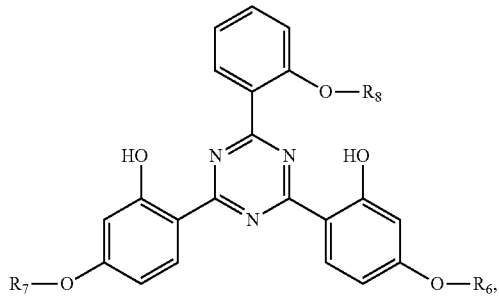
(2b)

the formula

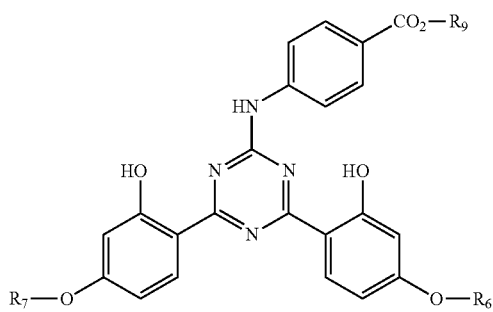
(3a)

or the formula

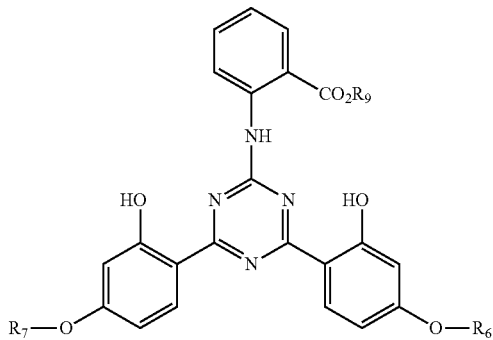
(3b)

in which

R$_6$ and R$_7$, independently of one another, are C$_3$-C$_{18}$alkyl; or —CH$_2$—CH(—OH)—CH$_2$—O-T$_1$;

R$_8$ is C$_1$-C$_{10}$alkyl or a radical of the formula

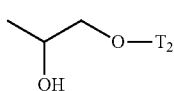
(2a$_1$)

or the formula

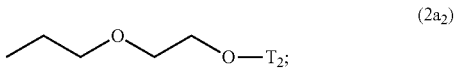
(2a$_2$)

R$_9$ is hydrogen; M; C$_1$-C$_5$alkyl; or a radical of the formula —(CH$_2$)$_m$—O-T$_2$;

T$_1$ and T$_2$, independently of one another, are hydrogen; or C$_1$-C$_5$alkyl; and m is 1 to 4.

Uppermost of interest are compounds of the formulae (2a) and (2b), in which

R$_6$ and R$_7$, independently of one another, are C$_3$-C$_{18}$alkyl; or —CH$_2$—CH(—OH)—CH$_2$—O-T$_1$;

R$_8$ is C$_1$-C$_{10}$alkyl;

and compounds of the formulae (3a) and (3b), in which

R$_6$ and R$_7$, independently of one another, are C$_3$-C$_{18}$alkyl or —CH$_2$—CH(—OH)—CH$_2$—O-T$_1$; and T$_1$ is hydrogen; or C$_1$-C$_5$alkyl.

Very particularly preferred in this case are triazine compounds of the formula (2) or (3), in which R$_6$ and R$_7$ have the same meaning.

Examples of compounds of the formula (1) which may be mentioned are:

2-(4'-methoxyphenyl)-4,6-bis(2'-hydroxy-4'-n-octyloxyphenyl)-1,3,5-triazine;

2,4-bis{[4-(3-(2-propyloxy)-2-hydroxypropyloxy)-2-hydroxy]phenyl}-6-(4-methoxyphenyl)-1,3,5-triazine;

2,4-bis{[4-(2-ethylhexyloxy)-2-hydroxy]phenyl}-6-[4-(2-methoxyethylcarboxyl)phenylamino]-1,3,5-triazine;

2,4-bis{[4-(tris(trimethylsiloxysilylpropyloxy)-2-hydroxy]phenyl}-6-(4-methoxyphenyl)-1,3,5-triazine;

2,4-bis{[4-(2"methylpropenyloxy)-2-hydroxy]phenyl}-6-(4-methoxyphenyl)-1,3,5-triazine;

2,4-bis{[4-(1',1',1',3',5',5',5'-heptamethyltrisilyl-2"-methylpropyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[4-ethylcarboxyl)-phenylamino]-1,3,5-triazine;

2,4-bis{[4-(2-ethylhexyloxy)-2-hydroxy]phenyl}-6-(1-methylpyrrol-2-yl)-1,3,5-triazine or 2,4-Bis{[4-(2-ethylhexyloxy)-2-hydroxy]phenyl}-6-(4-methoxyphenyl)-1,3,5-triazine.

Of special interest is the compound of formula (1)

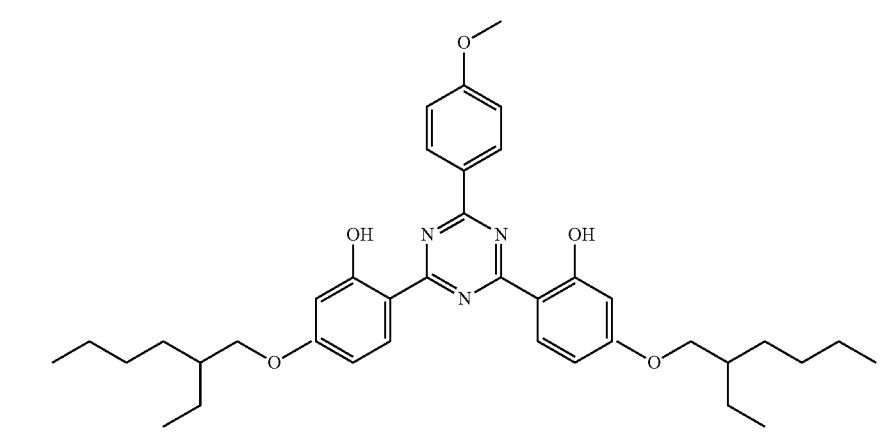
(1)

Surprisingly, the combination of these bisresorcinyl s-triazines gives an unexpected increase in UV absorbance in the UV-A region when combined with the zinc oxide particle distribution of the invention.

The weight ratio of the bisresorcinyl triazine, preferably the bisresorcinyl triazines of formula (2a), (2b), (3a) or (3b), most preferably bisresorcinyl triazines of formulas (2a) or (2b) and especially 2,4-Bis{[4-(2-ethylhexyloxy)-2-hydroxy]phenyl}-6-(4-methoxyphenyl)-1,3,5-triazine, to the zinc oxide coated particles can be virtually any ratio but preferable the ratio of zinc oxide to bisresorcinyl triazine will range from about 25:1 to 1:25 in the sunscreen formulation. Most typically however, the zinc oxide particles will exceed the weight of the bisresorcinyl triazine in the sunscreen formulation. For example the weight ratio of the zinc oxide to bisresorcinyl triazine will vary from about 25:1 to about 1:1 and most preferably 20:1 to about 5:1.

EXAMPLES

Formation of Zinc Oxide Powder According to the Invention

In the first step, high purity zinc metal is fed into a plasma arc, where it is vaporized. Oxygen is added to the zinc metal vapour to produce zinc oxide. The newly formed zinc oxide molecules then begin to associate with one another and nanocrystalline zinc oxide condenses from the vapor. These nanoparticles are then cooled rapidly in order to get them below their sintering temperature (to prevent particle size growth). In the dry state, the nanoparticles of ZnO associate with one another in loose, non-durable electrostatic agglomerates, which allows for handling and packaging of the product using traditional powder conveyance equipment. There are no other reactions, by-products, or waste streams.

The zinc oxide particles according to the invention (before coating) have a D50 mean particle distribution by volume determined by Dynamic Light Scattering of 580.8 nm. 0.0% of the particles in the distribution fall below 100 nm. The morphology of the crystal is zincite (hexagonal) and the average crystal size is 286.3 nm determined by X-Ray diffraction using the Scherrer equation.

Formation of Nanoparticulate Zinc Oxide Powder

The nanoparticles of zinc oxide are prepared as above except that an alternative distribution of the particles are gathered. The particles before coating have a D50 mean particle distribution by volume determined by Dynamic Light Scattering of 378 nm. 2.5% of the particles in the distribution fall below 100 nm. The morphology of the crystal is zincite (hexagonal) and the average crystal size is 69.6 nm determined by the X-Ray diffraction using the Scherrer equation.

Coating of the Zinc Oxide

In the second step, using different equipment, the zinc oxide according to the invention and the nanoparticulate zinc oxide is allowed to react with triethoxyoctyl silane monomer. In this reaction, the monomer reacts with itself on and around the surface of the zinc oxide producing ethanol as a by-product which is removed.

This reaction produces zinc oxide particles coated with poly-n-octylsilsesquioxane.

The coated and uncoated particles are shown to be discrete once formulated. The transparency of the zinc oxide dispersion before coating (in water) and after coating of the particles (in oil) is of comparable transparency (% transmission).

The coating makes up about 1 wt. % based on the total weight of the coated particle in both the zinc oxide powder of the invention and the nanoparticulate zinc oxide powder.

Example 1

Zinc oxide powder according to invention is produced in the first step, and then it is coated to make it hydrophobic in the second step.

Example 2

Nano particulate Zinc oxide powder is as produced in example 1 except the particle distribution falling below 100 nm, and the average crystal size determined by X-Ray diffraction using the Scherrer equation is different than that of example 1.

TABLE 1

| | Comparison of Zinc Oxide particles | | | | |
|---|---|---|---|---|---|
| Example | Distribution below 100 nm | Particle Distribution by Volume[1] | Crystal Size[2] | Morphology[3] | Wt. coating |
| 1 | 0.0% | 580.8 nm | 286.3 nm | Elongated/zincite (hexagonal) | 1% |
| 2 | 2.5% | 378 nm | 69.6 nm | Elongated/zincite (hexagonal) | 1% |

[1]$D_{50}$ by volume determined by Dynamic Light Scattering on a Malvern Nano ZS.
[2]Crystal size determined by XRD; Crystal Size by Scherrer equation.
[3]Morphology determined by Transmission Electron Microscopy and phase purity determined by X-ray diffraction.

Concentrated Dispersion of Zinc Oxide in Cosmetic Carrier 70 grams of poly-n-octylsilsesquioxane coated zinc oxide particles of example 1 are mixed vigorously with 30 grams of caprylic capric triglyceride as a cosmetically suitable carrier (Myritol® 312) to form a stable dispersion.

Application Formulations

Example 2

UV Defense Sun-Care Cream

SPF 15

| Ingredients | % w/w |
|---|---|
| Phase A | |
| Deionized Water | q/s |
| DC 193 Fluid (Dimethicone Copolyol)[2] | 0.10 |
| EDETA ® BD (Disodium EDTA)[1] | 0.10 |
| Phase B | |
| Glycerin (Glycerin)[3] | 3.00 |
| Keltrol CG (Xanthan Gum)[4] | 0.20 |
| Veegum Ultra (Magnesium Aluminum Silicate)[5] | 0.60 |
| Phase C | |
| Cremophor ® GS 32 (Polyglyceryl-3 Distearate)[1] | 3.00 |
| Cremophor ® A 20 (Ceteareth-20)[1] | 1.75 |
| Lanette O (Cetearyl Alcohol)[1] | 3.00 |
| Cetiol B (Dibutyl Adipate)[1] | 8.00 |
| Cetiol A (Hexyl Laurate)[1] | 5.00 |

-continued

| Ingredients | % w/w |
|---|---|
| UV CUT TiO2-55-AC(Titanium Dioxide and C12-15 Alkyl Benzoate and Cyclopentasiloxane and Stearic Acid and Polyhydroxystearic Acid and Alumina) [6] | 8.00 |
| Example 1 (Zinc Oxide and Triethoxycaprylysilane) [1] | 11.50 |
| Phase D | |
| Glydant Plus Liquid (DMDM Hydantoin (and) Iodopropynyl Butylcarbamate) [7] | 0.50 |
| Fragrance (Chamomile Fragrance 6109505) [8] | 0.05 |

Suppliers
[1] BASF
[2] Dow Corning Corp.
[3] Jeen
[4] CP Kelco
[5] R.T. Vanderbilt
[6] Grant
[7] Lonza Inc
[8] Bell Flavors and Fragrances Procedure:
Combine phase A, using propeller mixing, heat to 75-80° C.
Add phase B to phase A and mix well.
Combine phase C, heat to 75-80° C., and homogenize for 1-3 minutes.
Add phase C to phase NB using homogenizer and homogenize for 4-5 minutes.
Transfer to sweep mixing and cool to 40° C.
Add phase D to batch and mix well.
Cool to room temperature

Example 3

Baby Sunscreen Stick

SPF 30

| Ingredients | % w/w |
|---|---|
| Phase A | |
| Lipovol ® CO (*Ricinus Communis* (Castor) Seed Oil) [2] | q.s. |
| Cetiol ® SB-45 (*Butyrospermum Parkii* (Shea Butter)) [1] | 4.33 |
| White Beeswax SP422P (Beeswax) [3] | 6.00 |
| Candelilla Wax SP 75 (*Euphoria Cerifera* (Candelilla) wax) [3] | 6.00 |
| Ozokerite ®Wax Pastilles SP273 P (Ozokerite) [3] | 4.50 |
| Cetiol ® A (Hexyl Laurate) [1] | 2.13 |
| Cetiol ® SenSoft (Propylheptyl Caprylate) [1] | 3.26 |
| Phase B | |
| Lipovol ® CO (*Ricinus Communis* (Castor) Seed Oil) [2] | 10.00 |
| Cetiol ® B (Dibutyl Adipate) [1] | 4.60 |
| Pelemol ® PHS-8 (Polyhydroxystearic Acid) [4] | 0.50 |
| Uvinul ® MC 80 (Ethylhexyl Methoxycinnamate) [1] | 7.50 |
| Tinogard ® TL (Benzotriazolyl Dodecyl p-Cresol) [1] | 0.50 |
| Uvinul ® N 539T (Octocrylene) [1] | 5.50 |
| Lanette ® 18 (Stearyl Alcohol) [1] | 3.00 |
| Luvitol ® Lite (Hydrogenated Polyisobutene) [1] | 4.00 |
| Example 1 (Zinc Oxide and Triethoxycaprylylsilane) [1] | 11.50 |
| Tinogard ® TT (Pentaerythrityl Tetra-di-t-Buty Hydroxyhydrocinnamate) [1] | 0.05 |
| Cetiol ® RLF (Caprylyl-Caprylate Caprate) [1] | 4.50 |
| Vitamin E Acetate(Tocopheryl Acetate) [1] | 0.75 |
| Bisabolol Rac. (Bisabolol) [1] | 0.75 |
| Euxyl K 300 (Phenoxyethanol and Methylparaben and Ethylparaben and Butylparaben and Propylparaben and Isobutylparaben) [5] | 0.75 |

-continued

| Ingredients | % w/w |
|---|---|
| Dow Corning EP 9261 TI Cosmetic Powder (Dimethicone/Vinyl Dimethicone Crosspolymer and Titanium Dioxide) [6] | 1.50 |

Suppliers
[1] BASF
[2] Lipo
[3] Strahl & Pitsch
[4] Phoenix Chemical
[5] Schulke & Mayr
[6] Dow Corning Procedure:

Combine Phase A, mix well and heat to 85° C.

Combine Phase B and heat 85° C. while mixing, then homogenize till uniform.

Add Phase B to Phase A while at 85° C. and homogenize at low to medium speed for 3 minutes.

Transfer to mold while mixing and start cooling.

Start filling at 60-65° C.

Example 4

Soft Sunscreen Cream

SPF 15

| INGREDIENTS | % w/w |
|---|---|
| Phase A | |
| Cetiol ® SenSoft (Propylheptyl Caprylate) [1] | 5.00 |
| Uvinul ® MC 80 (Octinoxate) [1] | 7.50 |
| Cremophor ® WO7 (PEG-7 Hydrogenated Castor Oil) [1] | 3.50 |
| Luvitol ® Lite (Hydrogenated Polyisobutene) [1] | 5.00 |
| Example 1 (Zinc Oxide (and) Triethoxycaprylylsilane) [1] | 6.00 |
| Cremophor ® GS32 (Polyglyceryl-3 Distearate) [1] | 2.00 |
| Dehymulse ® LE (PEG-30 Dipolyhydroxystearate) [1] | 3.00 |
| Cetiol ® RLF (Caprylyl-Caprylate Caprate) [1] | 6.00 |
| White Beeswax SP-422P (Beeswax) [2] | 1.75 |
| Myritol ® 331 (Cocoglycerides) [1] | 5.00 |
| Vitamin E Acetate (Tocopheryl Acetate) [1] | 0.50 |
| Bisabolol, rac (Bisabolol) [1] | 0.20 |
| Dow Corning 556 (Phenyl Trimethicone) [4] | 2.00 |
| Phase B | |
| Deionized water | Q/S |
| Glycerin 99.7% (Glycerin) [3] | 2.00 |
| Dow Corning 193 C Fluid (PEG-12 Dimethicone) [4] | 1.00 |
| Salt (Sodium Chloride) [5] | 0.50 |
| Oristar ® MS (Magnesium Sulfate) [6] | 0.10 |
| Phase C | |
| Glydant Plus Liquid (DMDM Hydantoin Idopropynyl Butylcarbamate) [7] | 0.50 |
| Violet Amber and Sandalwood Fragrance F-138398 [8] | 0.20 |

Suppliers
[1] BASF
[2] Strahl & Pitsch
[3] Jeen
[4] Dow Corning
[5] Cargill
[6] Orient Stars
[7] Lonza Inc
[8] Intarome Procedure:
Combine phase A and heat to 75-80° C. and homogenize till smooth and uniform.
Combine phase B and heat to 75-80° C.
Add Phase B to Phase A while at 75-80° C. and homogenize for 1-3 minutes at low/medium speed.
Transfer to sweep mixing and start cooling.
Add Phase C at 40° C. or below one by one, mix well then stop.

Example 5

Daily Wear SPF Treatment

Estimated SPF 30

| Ingredients | % w/w |
|---|---|
| Phase A | |
| Deionized Water | q.s. |
| D-Panthenol 75W (Panthenol) [1] | 0.75 |
| EDTA BD (Disodium EDTA) [1] | 0.10 |
| Phase B | |
| Glycerin (Glycerin 99%) [2] | 2.00 |
| Keltrol ® CG (Xantham Gum) [3] | 0.25 |
| Veegum ® Ultra (Magnesium Aluminum Silicate) [4] | 0.35 |
| Phase C | |
| Lanette ® 22 (Behenyl Alcohol) [1] | 2.00 |
| Cremophor ® GS 32 (Polyglyceryl-3 Distearate Gum) [1] | 1.75 |
| Emulgade ® PL 68/50 (Cetearyl Glucoside and Cetearyl Alcohol) [1] | 2.75 |
| Cremophor ® WO-7 (PEG-7 Hydrogenated Castor Oil) [1] | 0.20 |
| Myritol ® 331 (Cocoglycerides) [1] | 3.50 |
| Uvinul ® 539T (Octocrylene) [1] | 4.00 |
| Cetiol ® OE (Dicaprylyl Ether) [1] | 3.00 |
| Phase D | |
| Example 1 (Zinc Oxide and Triethoxycaprylysilane) [1] | 11.50 |
| Uvinul ® MC 80 (Ethylhexyl Methoxycinnamate) [1] | 7.50 |
| Cetiol ® RLF (Caprylyl-Caprylate Caprate) [1] | 3.50 |
| Cetiol ® Sensoft (Propylhetyl Caprylate) [1] | 3.50 |
| Phase E | |
| Jeecide ® P (Phenoxyethanol and Methylparaben and Ethylparaben and Butylparaben and Propylparaben and Isobutylparaben) [2] | 0.75 |
| Marine Filling Spheres (Pentaerytrityl Tetraisostearate and Silica Dimethyl Sylilate and Sodium Chondroitin Sulfate and Atelocollagen and Butylene Glycol) [1] | 1.00 |
| Deliner (Zea Mays (Corn) Kernel Extract and Butylene Glycom and Xanthan Gum) [1] | 1.00 |
| Fragrance (Unisex Fragrance #2 for Skin Care) [5] | 0.10 |

Suppliers
[1] BASF
[2] Jeen
[3] CP Kelco
[4] RT Vanderbilt
[5] Intarome

Procedure:
Combine Phase A and start heating to 75-80° C.
Premix Phase B and add to Phase A while heating to 75-80° C.
Combine Phase C and heat to 75-80° C.
Combine Phase D homogenize until smooth and heat to 75-80° C.
Add Phase D to Phase C while at 75-80° C. and homogenize for 1-3 minutes.
Add Phase C/D to batch under homogenization, and homogenize until uniform
Transfer to sweep mixing and start cooling
Add Phase E ingredients one by one and mix well between additions
Cool to room temperature and stop.

Comparative Study

Six sunscreen formulations are compared all using the same basic formulation.

TABLE 2

| Sunscreen Formulations for Comparative Study | | | | | | | |
|---|---|---|---|---|---|---|---|
| Chemical Name | INCI | Cont | 1 | 2 | 3 | 4 | 5 |
| DI Water | | q.s. | q.s. | q.s. | q.s. | q.s | q.s |
| Edeta BD | Disodium EDTA | 0.1 | 0.1 | 0.1 | 0.1 | 0.1 | 0.1 |
| Pluracare ® E 400 NF Polyethylene[1] | PEG-8 | 1.25 | 1.25 | 1.25 | 1.25 | 1.25 | 1.25 |
| Keltrol ® CG[2] | Xanthum Gum | 0.3 | 0.3 | 0.3 | 0.3 | 0.3 | 0.3 |
| Vegum ® Ultra[3] | Hydrated Magnesium Aluminum Silicate | 0.7 | 0.7 | 0.7 | 0.7 | 0.7 | 0.7 |
| Glycerin 95% | Glycerin | 2 | 2 | 2 | 2 | 2 | 2 |
| Cremophor ® A6[1] | Cethearth-6 stearyl Alcohol | 1.5 | 1.5 | 1.5 | 1.5 | 1.5 | 1.5 |
| Cremophor ®A25[1] | Ceteareth-25 | 1.5 | 1.5 | 1.5 | 1.5 | 1.5 | 1.5 |
| Luvitol ® Lite[1] | Hydrogenated polyisobutene | 5 | 5 | 5 | 5 | 5 | 5 |
| Myritol ® 331[1] | Glyceryl Caprylate/Caprate/Cocoate | 5 | 5 | 5 | 5 | 5 | 5 |
| Lanette ® O[1] | Cetostearyl alcohol | 2.5 | 2.5 | 2.5 | 2.5 | 2.5 | 2.5 |
| Cetiol ® RLF[1] | Caprylyl Caprylate/Caprate | 0.5 | 0.5 | 0.5 | 0.5 | 0.5 | 0.5 |
| Inventive Zinc Oxide | Zinc Oxide (and) Triethoxycaprylylsilane | | 15 | | 15 | | |
| Zinc Oxide - nanoparticle distribution | Zinc Oxide (and) Triethoxycaprylylsilane | | | | | 15 | 15 |
| Tinosorb ® S[1] | Bemotrizinol | | | 2 | 2 | | 2 |
| Euxyl ® K300[4] | Propylparaben and Isobutylparaben | 0.75 | 0.75 | 0.75 | 0.75 | 0.75 | 0.75 |

TABLE 2-continued

Sunscreen Formulations for Comparative Study

| Chemical Name | INCI | Cont | 1 | 2 | 3 | 4 | 5 |
|---|---|---|---|---|---|---|---|
| Luvigel ® Star[1] | Polyurethane-39 | 2.5 | 2.5 | 2.5 | 2.5 | 2.5 | 2.5 |
| pH adjuster | | q.s. | q.s | q.s. | q.s. | q.s. | q.s. |
| Total | | 100 | 100 | 100 | 100 | 100 | 100 |

Suppliers
[1]BASF
[2]CP Kelco
[3]RT Vanderbilt
[4]Schulke & Mayr GmbH

The control contains no UV absorber (control).

Formulation 1 contains 15 wt. % of the zinc oxide of example 1.

Formulation 2 contains Tinosorb® S at 2 wt. % but no zinc oxide.

Formulation 3 contains 15 wt. percent zinc oxide of example 1 and 2 wt. % Tinosorb® S.

Formulation 4 contains 15 wt. % of zinc oxide wherein the particle distribution is as in example 2.

Formulation 5 contains 15 wt. % of zinc oxide wherein the particle distribution is as in example 2 and 2 wt. % Tinosorb® S.

PMMA plates are coated with ~0.75 mg/cm$^2$ sample formulations and glycerin for the control. The absorbance spectrum from 290 nm to 400 nm is compared for the control and each sample using a Labsphere 2000S following the FDA Sunscreen Analysis (2011) protocol.

The raw instrument data are averaged over 9 locations on each test plates to obtain the average absorbance. For each sample, the absorbance of the formulation without any sunscreens is deducted from the data to correct for any background (assuming linearity).

The excess absorbance for formulation 3 is determined by taking the absorbance of the formulation 3 (containing both the zinc oxide of example 1 and Tinosorb® S), then deducting the absorbances of the formulations 1 and 2.

The excess absorbance is clearly positive in the formulation 3 containing both the zinc oxide of example 1 and Tinosorb® S at wavelengths above 370 nm (in the UVA region).

The excess absorbance is also determined for formulation 5 (containing nanoparticulate zinc oxide and Tinosorb® S) in a similar way as above.

The excess absorbance for formulation 5 is determined by taking the absorbance of the formulation 5 (containing both the zinc oxide of example 2 and Tinosorb® S), then deducting the absorbances of the formulations 4 and 2.

The excess absorbance is clearly positive in the formulation 3 containing both the zinc oxide of example 1 and Tinosorb® S at wavelengths above 370 nm (in the UVA region).

There is also an excess of absorbance in the formulation 5 at wavelengths above 380 nm (but not as significant as that shown by the inventive combination of formula 5). But more significantly there is a clear lower absorbance performance in the range from 290 nm to 375 nm for formulation 5 when compared to formulation 3.

The results are given in Table 3 below.

TABLE 3

UV Absorbance Values Determined Absorbance of Formulation 3 - Formulation 2 Formulation 1

| Wavelength (nm) | Cont | 1 (ex. 1) | 2 (Tin. S) | 3 ex. 1 + Tin S) | Excess Ab. (formulation 3 - formulation 1 - formulation 2) | 5 (ex. 2) | 6 (ex. 2 + Tin S) | Excess Ab. (formulation 5 - formulation 4 - formulation 2 |
|---|---|---|---|---|---|---|---|---|
| 290 | 0.4 | 46.0 | 39.7 | 81.1 | −4.5 | 61.8 | 87.0 | −14.5 |
| 295 | 0.6 | 45.4 | 45.4 | 86.9 | −3.8 | 60.8 | 91.2 | −15.0 |
| 300 | 1.8 | 43.0 | 47.8 | 89.5 | −1.3 | 58.5 | 93.1 | −13.2 |
| 305 | 1.9 | 43.1 | 51.8 | 93.7 | −1.2 | 58.3 | 96.3 | −13.9 |
| 310 | 1.5 | 44.0 | 54.5 | 96.5 | −2.0 | 58.7 | 97.8 | −15.4 |
| 315 | 2.4 | 42.2 | 51.3 | 93.3 | −0.3 | 57.0 | 95.1 | −13.2 |
| 320 | 2.7 | 41.7 | 49.4 | 91.3 | 0.2 | 56.3 | 93.4 | −12.3 |
| 325 | 2.6 | 41.9 | 48.9 | 90.8 | −0.1 | 56.3 | 92.8 | −12.4 |
| 330 | 2.7 | 41.9 | 48.6 | 90.5 | 0.0 | 56.1 | 92.5 | −12.3 |
| 335 | 2.4 | 42.5 | 49.7 | 91.7 | −0.6 | 56.6 | 93.2 | −13.1 |
| 340 | 2.5 | 42.4 | 50.1 | 92.2 | −0.3 | 56.5 | 93.7 | −12.9 |
| 345 | 2.2 | 43.3 | 51.3 | 93.5 | −1.0 | 57.3 | 94.8 | −13.8 |
| 350 | 2.4 | 43.3 | 50.8 | 93.3 | −0.8 | 57.6 | 94.9 | −13.5 |
| 355 | 2.3 | 44.0 | 50.7 | 93.7 | −1.0 | 58.7 | 95.5 | −14.0 |
| 360 | 2.0 | 45.4 | 50.2 | 93.9 | −1.6 | 60.9 | 96.2 | −14.9 |
| 365 | 2.4 | 45.7 | 45.8 | 90.8 | −0.8 | 61.7 | 94.2 | −13.4 |
| 370 | 2.3 | 47.3 | 39.0 | 85.6 | −0.6 | 62.8 | 89.6 | −12.2 |
| 375 | 2.4 | 46.0 | 27.6 | 74.4 | 0.9 | 54.9 | 75.0 | −7.5 |
| 380 | 2.3 | 35.1 | 15.6 | 54.6 | 3.8 | 33.7 | 49.8 | 0.5 |
| 385 | 2.5 | 24.7 | 6.0 | 38.6 | 7.8 | 22.3 | 33.6 | 5.4 |
| 390 | 2.3 | 22.0 | 1.0 | 30.3 | 7.3 | 18.9 | 25.2 | 5.2 |

TABLE 3-continued

UV Absorbance Values Determined Absorbance of Formulation 3 - Formulation 2 Formulation 1

| Wavelength (nm) | Cont | 1 (ex. 1) | 2 (Tin. S) | 3 ex. 1 + Tin S) | Excess Ab. (formulation 3 - formulation 1 - formulation 2) | 5 (ex. 2) | 6 (ex. 2 + Tin S) | Excess Ab. (formulation 5 - formulation 4 - formulation 2) |
|---|---|---|---|---|---|---|---|---|
| 395 | 2.7 | 19.9 | −2.9 | 24.3 | 7.3 | 16.5 | 19.6 | 6.1 |
| 400 | 2.9 | 19.0 | −4.7 | 21.3 | 7.0 | 15.0 | 16.5 | 6.1 |

The invention claimed is:

1. A sunscreen composition comprising:
   a) zinc oxide particles defined by a mean particle size (volume) distribution of about 400 nm to about 650 nm, the zinc oxide particles having a hexagonal zincite crystal structure;
   wherein the zinc oxide particles are formed by vaporizing zinc metal in a plasma system to form a zinc metal vapor and adding oxygen to the zinc metal vapor, the zinc oxide particles being formed without milling, the formed zinc oxide particles remaining discrete particles after formation, and the zinc oxide particles having a hydrophobic coating; and
   0.0% of the zinc oxide particles fall below 100 nm and percentage (%) is based on a number of particles in the distribution; and
   b) optionally, a cosmetically acceptable carrier.

2. The sunscreen composition of claim 1, the zinc oxide particles having an average crystal size of about 150 nm to about 350 nm.

3. The sunscreen composition of claim 1, wherein the zinc oxide particles are present in an amount of about 0.1 to about 25 wt. % of the sunscreen composition.

4. The sunscreen composition of claim 1, wherein the cosmetically acceptable carrier is a hydrophobic liquid suitable for skin contact, the cosmetically acceptable carrier further comprising at least one adjuvant selected from the group consisting of surfactants, super-fatting agents, emulsifiers, consistency regulators, thickeners, polymers, biogenic active ingredients, swelling agents, additional UV screen agents, antioxidants, hydrotropic agents, preservative, solubilizers, perfume oils, colorants, bacteria-inhibiting agents, and mixtures thereof.

5. The sunscreen composition of claim 4, wherein the adjuvant is an organic UV screen agent selected from a group defined by formulae

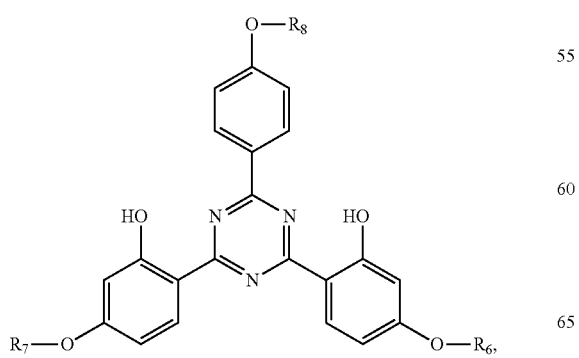

(2a)

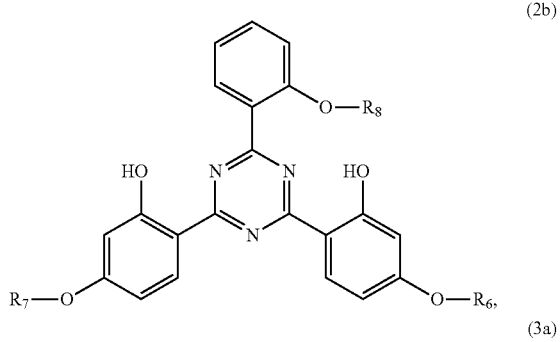

(2b)

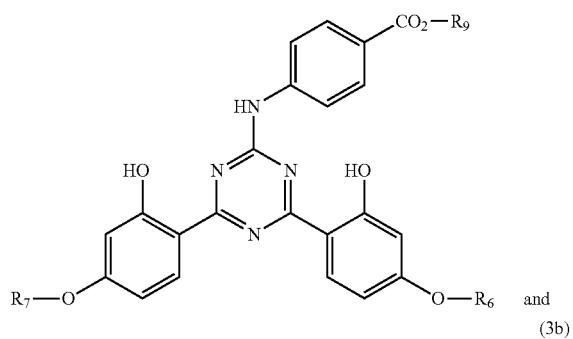

(3a)

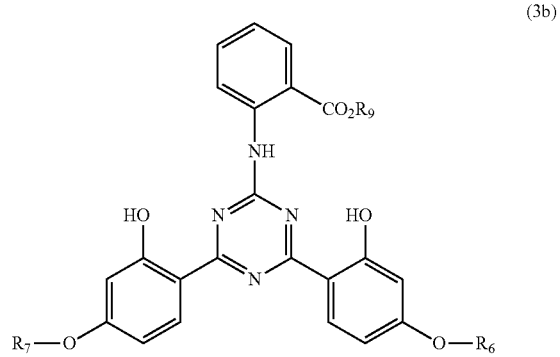

and (3b)

in which $R_6$ and $R_7$, independently of one another, are C3-C18 alkyl or —$CH_2$—CH(—OH)—$CH_2$—O-$T_1$;

$R_8$ is C1-C10 alkyl or a radical of formula

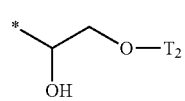

(2a-1)

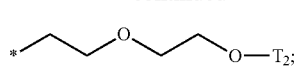
(2a-2)

the mark * is a single bond $R_9$ is hydrogen, M, C1-C5 alkyl, or a radical of formula —$(CH_2)m$-O-$T_2$;

M is a metal cation;

$T_1$ and $T_2$ independently of one another are hydrogen, or C1-C5 alkyl; and m is 1 to 4.

6. The sunscreen composition according to claim 1, wherein the hydrophobic coating is an organosilicon compound.

7. The sunscreen composition according to claim 1, wherein the hydrophobic coating on the zinc oxide particles is present in an amount from 0.01 to about 5 wt. % based on a total weight of the coated zinc oxide particles.

8. The sunscreen composition according to claim 7, wherein the hydrophobic coating is a polysiloxane.

9. The sunscreen composition according to claim 1, wherein the composition is provided in a form of a cream, a gel, a lotion, an emulsion, stick preparations, powders, or ointments.

10. A dispersion comprising
   a) the zinc oxide particles according to claim 1, and
   b) a cosmetically acceptable carrier selected from a group comprising, C6-C18 fatty acids esters of di- or triglycerides, modified by r action with other alcohols, fatty acids esters of polyglycerol, hydrogenated vegetable oil, sweet almond oil, wheat germ oil, sesame oil, hydrogenated cottonseed oil, coconut oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, and borage oil; wherein the zinc oxide particles are present in an amount of at least about 50 to about 90 weight percent by total weight of the dispersion.

11. A method of formulating a sunscreen composition by adding the zinc oxide particles according to claim 1 to a cosmetically acceptable carrier, wherein the cosmetically acceptable carrier is a hydrophobic liquid suitable for skin contact.

* * * * *